(12) United States Patent
Lee et al.

(10) Patent No.: US 9,024,073 B2
(45) Date of Patent: *May 5, 2015

(54) THIO COMPOUNDS AND PREPARING METHOD OF THE SAME

(75) Inventors: Hyung Jae Lee, Daejeon (KR); Chang Kyo Shin, Daejeon (KR); Jin Eok Kim, Daejeon (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 251 days.

This patent is subject to a terminal disclaimer.

(21) Appl. No.: 13/394,730

(22) PCT Filed: Aug. 31, 2010

(86) PCT No.: PCT/KR2010/005885
§ 371 (c)(1),
(2), (4) Date: Mar. 7, 2012

(87) PCT Pub. No.: WO2011/031031
PCT Pub. Date: Mar. 17, 2011

(65) Prior Publication Data
US 2012/0172628 A1    Jul. 5, 2012

(30) Foreign Application Priority Data

Sep. 10, 2009 (KR) .................. 10-2009-0085477

(51) Int. Cl.
*C07C 319/00* (2006.01)
*C07C 321/00* (2006.01)
*C07C 323/00* (2006.01)
(Continued)

(52) U.S. Cl.
CPC .............. *C08K 5/375* (2013.01); *C07C 323/16* (2013.01); *C07C 2103/68* (2013.01); *C08G 8/30* (2013.01); *C08L 61/18* (2013.01)

(58) Field of Classification Search
CPC .. C07C 323/00; C07C 2102/42; C07C 323/13
See application file for complete search history.

(56) References Cited

U.S. PATENT DOCUMENTS 3,565,857 A * 2/1971 Spacht ........................ 524/331
8,729,169 B2 * 5/2014 Lee et al. ..................... 524/325
2001/0044518 A1 11/2001 Hoffmann et al.

FOREIGN PATENT DOCUMENTS

CA       2029708      7/2003
WO   2007/042418    4/2007

OTHER PUBLICATIONS

International Search Report mailed Oct. 18, 2010 for PCT/KR2010/005885, citing the above references.
Written opinion of ISA mailed Oct. 18, 2010 for PCT/KR2010/005885, citing the above references.
(Continued)

*Primary Examiner* — Clinton Brooks
(74) *Attorney, Agent, or Firm* — Lowe Hauptman & Ham, LLP (57) ABSTRACT

Provided are novel thio compounds and a method for preparing the same. More particularly, there is provided a novel thio compound prepared by reacting an alkylation product of p-cresol and dicyclopentadiene with mercaptan and paraformaldehyde. Unlike existing antioxidants such as 2,6-di-t-butyl-4-methylphenol (BHT) being harmful to the human body due to the high volatility, the novel thio compounds of the present invention, which have the low volatility because of their high molecular weight, give no harm to the human body. Further, with excellent performances, they are suitable to replace the existing antioxidants.

13 Claims, 4 Drawing Sheets

A

B

C (51) Int. Cl.
*C07C 381/00* (2006.01)
*C08K 5/375* (2006.01)
*C07C 323/16* (2006.01)
*C08G 8/30* (2006.01)
*C08L 61/18* (2006.01)

(56) References Cited

OTHER PUBLICATIONS

International Preliminary Report on Patentability for PCT/KR2010/005885 (cited references have been previously filed on Mar. 7, 2012).

* cited by examiner

THIO COMPOUNDS AND PREPARING METHOD OF THE SAME

CROSS REFERENCE TO RELATED APPLICATION

This application claims the priority of Korean Patent Application No. 10-2009-0085477, filed on Sep. 10, 2009 in the KIPO (Korean Intellectual Property Office). Further, this application is the National Phase application of International Application No. PCT/KR2010/005885, filed on Aug. 31, 2010, which designates the United States and was published in English.

TECHNICAL FIELD

The present invention relates to thio compounds prepared by reacting an alkylation product of p-cresol and dicyclopentadiene with mercaptan and paraformaldehyde.

BACKGROUND

At present, phenol-, amine-, phosphite- and thioester-based antioxidants are used to prevent oxidative degradation of polymers. These antioxidants may be used alone or in combination, and they have their own limitations. Specifically, although phenol-based antioxidants have good thermal stability initially, their use is limited because they tend to be colored after oxidation. Amine-based antioxidants exhibit excellent performance, but they have inherent colors. And, phosphite-based antioxidants are not only subject to hydrolysis upon contact with water but also to decomposition during vulcanization for rubber synthesis. Thioester-based antioxidants do not fully exert their performance when used alone and need other primary antioxidants.

Although 2,6-di-t-butyl-4-methylphenol (BHT), which is commonly added to polymers has good thermal stability as a primary antioxidant, it is volatile because of its low molecular weight. As a result, the performance of heat-resistant additives decreases and severe discoloration may occur. Particularly, BHT is known to affect the liver and may cause allergies and tumors.

Because of the environmental pollution problem of the volatile BHT, BHT-free polymer products are demanded by industries. Accordingly, there is an urgent need for the development of an antioxidant not harmful to humans and less volatile while being capable of preventing oxidation of polymers and maintaining physical properties thereof.

Although 1076 (octadecyl-3-(3,5-di-t-butyl-4-hydroxyphenyl)-propionate), 1010 (pentaerythrityl-tetrakis[3-(3,5-di-t-butyl-4-hydroxyphenyl)-propionate]), or the like are used as replacements for BHT, they require the addition of secondary antioxidants since they are limited in performance as primary antioxidants and physical properties.

DISCLOSURE

Technical Problem

The inventors of the present invention have made effort for the development of a multifunctional phenolic antioxidant with improved antioxidant activities capable of replacing 2,6-di-t-butyl-4-methylphenol (BHT). As a result, it has been discovered that a novel thio compound can be useful as both primary and secondary antioxidants, by adding mercaptan to oligomers of p-cresol and dicyclopentadiene used to increase the molecular weight for the purpose of solving the volatility problem.

Accordingly, the present invention is directed to providing the novel thio compounds and a method for preparing the same.

Technical Solution

In one aspect, the present invention relates to a thio compound represented by Chemical Formula 1:

wherein $R_1$ is $-CH_2SR_2$, $R_2$ is a linear-, branched- or cyclic alkyl group of $C_5$-$C_{16}$ or an aromatic group of $C_6$-$C_{16}$; and n is a real number satisfying $1 \leq n \leq 20$.

In another aspect, the present invention relates to a method for preparing a thio compound, including: reacting p-cresol with dicyclopentadiene to prepare an alkylation product represented by Chemical Formula 2; and reacting the alkylation product represented by Chemical Formula 2 with mercaptan represented by $R_2SH$ and paraformaldehyde to prepare a thio compound represented by Chemical Formula 1:

wherein n is a real number satisfying $1 \leq n \leq 20$; and wherein $R_1$ is $-CH_2SR_2$, wherein $R_2$ is a linear-, branched- or cyclic alkyl group of $C_5$-$C_{16}$ or an aromatic group of $C_6$-$C_{16}$; and n is a real number satisfying $1 \leq n \leq 20$.

In another aspect, the present invention relates to an antioxidant including the thio compound as an effective ingredient.

3

Advantageous Effects

Unlike commercially available antioxidants such as 2,6-di-t-butyl-4-methylphenol (BHT) being harmful to the human body due to the high volatility, the novel thio compounds of the present invention, which have the low volatility because of their high molecular weight, give no harm to the human body. Further, with excellent performances, they are suitable to replace the existing antioxidants.

Other features and aspects will be apparent from the following detailed description, drawings, and claims.

BRIEF DESCRIPTION OF DRAWINGS

The above and other objects, features and advantages of the present invention will become apparent from the following description of preferred embodiments given in conjunction with the accompanying drawings, in which.

MODE FOR INVENTION

The advantages, features and aspects of the present invention will become apparent from the following description of the embodiments with reference to the accompanying drawings, which is set forth hereinafter. The present invention may, however, be embodied in different forms and should not be construed as limited to the embodiments set forth herein. Rather, these embodiments are provided so that this disclosure will be thorough and complete, and will fully convey the scope of the present invention to those skilled in the art. The terminology used herein is for the purpose of describing particular embodiments only and is not intended to be limiting of example embodiments. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Hereinafter, the present invention will be described in more detail.

The present invention relates to a thio compound represented by Chemical Formula 1:

[Chemical Formula 1]

wherein $R_1$ is $-CH_2SR_2$, $R_2$ is a linear-, branched- or cyclic alkyl group of $C_5$-$C_{16}$ or an aromatic group of $C_6$-$C_{16}$; and n is a real number satisfying $1 \leq n \leq 20$. Preferably, $R_2$ is a linear-, branched- or cyclic alkyl group of $C_6$-$C_{16}$, more preferably a linear or branched alkyl group of $C_5$-$C_{12}$. And, preferably n is a real number satisfying $1 \leq n \leq 12$, more preferably a real number satisfying $1 \leq n \leq 6$.

Preferably, the thio compound of the present invention has a number average molecular weight ($M_n$) of 400 to 5,000, more preferably 400 to 3,000. If the number average molecular weight of the thio compound of the present invention is smaller than 400, the compound may be volatile. Meanwhile, if the number average molecular weight exceeds 5,000, the desired thio compound may not be obtained. Therefore, it is preferred that the average molecular weight range described above be maintained.

The thio compound of the present invention is prepared by two steps: a first step is a reaction of p-cresol with dicyclopentadiene to prepare an alkylation product represented by Chemical Formula 2; and a second step is a reaction of the alkylation product represented by Chemical Formula 2 with mercaptan represented by $R_2SH$ and paraformaldehyde to prepare a thio compound represented by Chemical Formula 1:

(2)

wherein n is a real number satisfying $1 \leq n \leq 20$; and (1)

wherein $R_1$ is $-CH_2SR_2$, $R_2$ is a linear-, branched- or cyclic alkyl group of $C_5$-$C_{16}$ or an aromatic group of $C_6$-$C_{16}$; and n is a real number satisfying $1 \leq n \leq 20$.

In the first step of preparing for the alkylation product, p-cresol is reacted with dicyclopentadiene by Friedel-Crafts alkylation to give the alkylation product represented by Chemical Formula 2. Preferably, p-cresol is used in an equivalent of 1 to 10, more preferably an equivalent of 2 to 5, based on 1 equivalent of dicyclopentadiene. Beyond the above range, the performance may be not good. Therefore, it is preferred that the above range be maintained.

The reaction of the first step is performed in the presence of an acid catalyst. Preferably, the acid catalyst is one or more metal halide(s) selected from $AlCl_3$, $AlBr_3$, $AlI_3$, $TiCl_4$, $SnCl_4$, $FeCl_3$, $ZnCl_2$ and $ZrCl_4$; one or more inorganic acid(s) selected from $H_2SO_4$, $H_3PO_4$ and HF; and Lewis acid catalyst such as $BF_3$. Preferably, the acid catalyst is used in an amount of 0.1 to 5 wt % based on the total weight of p-cresol and dicyclopentadiene. If the acid catalyst is used less than 0.1 wt %, too long a reaction time is required. Meanwhile, if it is used more than 5 wt %, a lot of byproducts may be produced. Therefore, it is preferred that the above range be maintained.

Preferably, the reaction of the first step is performed at 25 to 160° C. for 1 to 10 hours, more preferably at 80 to 150° C. for 2 to 8 hours. If the reaction is preformed at a temperature below 25° C., the reaction may not proceed smoothly leading to incomplete reaction. Meanwhile, if the reaction is preformed at a temperature above 160° C., the reaction may proceed well, but produce many byproducts, thus reducing the economic efficiency. Further, if the reaction is carried out for less than 1 hour, the reaction may be incomplete. Meanwhile, if the reaction is conducted for more than 10 hours, the economic efficiency may be reduced.

The first step may further comprise a process of concentrating the alkylation products at 100 to 200° C. under a pressure of 1 to 50 mmHg.

In the second step of preparing the thio compounds, a mercaptan represented by $R_2SH$ may be used in an equivalent of 2 to 4, preferably an equivalent of 2 to 3, based on 1 equivalent of the alkylation product. In addition, paraformaldehyde may be used in an equivalent of 2 to 4, preferably an equivalent of 2 to 3, based on 1 equivalent of the alkylation product. If the addition amount of mercaptan and paraformaldehyde is less than 2 equivalents, respectively, a mixture of a monothio compound and a dithio compound may be yielded. And, if it exceeds 4 equivalents, a lot of byproducts are produced and then a complicate process may be required for purification. $R_2$ of the mercaptan may be a linear-, branched-, cyclic- or aromatic alkyl group of $C_6$-$C_{16}$, preferably a linear- or branched alkyl group of $C_6$-$C_{16}$, more preferably one having 8 to 12 carbon atoms. If $R_2$ has less than 6 carbon atoms, a mercaptan of $R_2SH$ separated from thio compounds by decomposition may cause to give a deep smell easily. Meanwhile, if it has more than 16 carbon atoms, the reactivity with the alkylation products may decrease. Specific examples of the mercaptan include octyl mercaptan, decyl mercaptan, dodecyl mercaptan, benzyl mercaptan, thiophenol, or the like.

The reaction of the second step is performed in the presence of a base catalyst or a catalyst mixture of a base catalyst and an acid catalyst. The base catalyst is not particularly limited but an amine-based catalyst is preferred. Specifically, one or more selected from piperidine, pyrrolidine, piperazine, dimethylamine, diethylamine and benzylmethylamine may be used. The base catalyst may be used in an equivalent of 0.1 to 0.6, preferably an equivalent of 0.2 to 0.5, based on 1 equivalent of the alkylation products. If the base catalyst is used less than 0.1 equivalent, the reaction time may increase. Meanwhile, if it is used more than 0.6 equivalent, reaction time decreases but a lot of byproducts are produced. Therefore, it is preferred that the above range be maintained.

In the case of a catalyst mixture of a base and an acid, the acid catalyst may be one or more selected from an organic- and an inorganic acid. Specifically, the organic acid may be an aliphatic- or aromatic organic acid having one or more functional group(s) selected from carboxylate, sulfate, and phosphate; or an aliphatic organic acid or aromatic organic acid having one or more functional group(s) selected from alkyl, alkenyl, aryl, hydroxyl, thiol, ether, ester, ketone and aldehyde and one or more functional group(s) selected from carboxylate, sulfate and phosphate at the same time. Further, the inorganic acid may be one or more heterogeneous acid selected from sulfuric acid, phosphoric acid, and two or more oxygen acids. The heterogeneous acids, which are applied to clay, cation exchange resin, or the like, may be used as complex inorganic acids. In the catalyst mixture, the acid catalyst may be used in an equivalent of 0.1 to 0.9, preferably an equivalent of 0.4 to 0.8, based on 1 equivalent of the base catalyst. If it is used less than 0.1 equivalent, the effect of acid may be not exerted any more. Meanwhile, if it is used more than 0.9 equivalent, it may reduce the effect of the base catalyst. Therefore, it is preferred that the above range be maintained.

In the second step, the alkylation products represented by Chemical Formula 2, the mercaptan represented by $R_2SH$, paraformaldehyde and the base catalyst or the catalyst mixture are added to a reaction solvent and the reaction is carried out. The reaction is performed in a reaction solvent which may be toluene or a 1:10 to 100, preferably 1:30 to 70, mixture of water and toluene based on weight. The reaction solvent may be used in an amount of 50 to 200 parts by weight, more preferably 80 to 150 parts by weight, based on 100 parts by the total weight of the reactants comprising the alkylation product represented by Chemical Formula 2, the mercaptan represented by $R_2SH$, paraformaldehyde and the base catalyst or the catalyst mixture. If the reaction solvent is used less than 50 parts by weight, it may be difficult to stir. Meanwhile, if it is used more than 200 parts by weight, the incomplete reaction may occur or the reaction rate may decrease. Therefore, it is preferred that the above range be maintained.

In the second step, the reaction may be performed at 50 to 150° C. for 1 to 6 hours, more preferably at 90 to 120° C. for 2 to 4 hours. If the reaction is conducted at a temperature below 50° C., incomplete reaction may occur. Meanwhile, if the temperature exceeds 150° C., the reaction may proceed well and discoloration will not occur, but the process may not be cost effective. Further, if the reaction is conducted for less than 1 hour, incomplete reaction may occur. Meanwhile, if the reaction is conducted for more than 6 hours, the economic efficiency may decrease although discoloration will be prevented.

EXAMPLES

The examples and experiments will now be described. The following examples and experiments are for illustrative purposes only and not intended to limit the scope of this disclosure.

Synthesis Example 1

Preparation of Alkylation Product p-Cresol (324 g) and $BF_3$ ether solution (boron trifluoride etherate, 5.5 g) were mixed and heated to 90° C. After slowly adding dicyclopentadiene (132 g) for 1 hour, followed by reaction for 3 hours, the resulting reaction solution was concentrated at 190° C. under a pressure of 15 mmHg to give alkylation products (300 g).

Example 1

Preparation of Octylthio Compounds Represented by Chemical Formula 1-1

(1-1)

The alkylation products (1 equivalent) prepared in Synthesis Example 1 was dissolved in toluene of the same amount. Then, after adding paraformaldehyde (2 equivalent), octyl mercaptan (2 equivalent), and dimethylamine (0.2 equivalent), reaction was carried out at 100° C. for 3 hours. The organic layer separated from the reaction product was concentrated under reduced pressure to give octylthio compounds as a light-brown liquid. Conversion and purity were measured by HPLC. The result is given in Table 1.

Example 2

Octylthio compounds were prepared in the same manner as Example 1, except for using a catalyst mixture of diethylamine and acetic acid instead of the base catalyst dimethylamine. The result is also given in Table 1.

Example 3

Preparation of Decylthio Compound Represented by Chemical Formula 3-1

(3-1)

Decylthio compounds were prepared in the same manner as Example 1, except for using decyl mercaptan instead of octyl mercaptan and using a catalyst mixture of piperidine and phosphoric acid instead of the base catalyst dimethylamine. The result is also given in Table 1.

Example 4

Preparation of Dodecylthio Compound Represented by Chemical Formula 4-1

(4-1)

Dodecylthio compounds were prepared in the same manner as Example 1, except for using dodecyl mercaptan instead of octyl mercaptan and using a catalyst mixture of piperidine and propanoic acid instead of the base catalyst dimethylamine. The result is also given in Table 1.

TABLE 1

| | mercaptans | Catalyst (equivalents) | Reaction condition | Conversion (%) | Purity (%) |
|---|---|---|---|---|---|
| Example 1 | octyl mercaptan | Dimethylamine (0.2) | 100° C., 3 hours | 95 | 95 |
| Example 2 | octyl mercaptan | Dimethylamine (0.2), acetic acid (0.15) | 100° C., 3 hours | 97 | 97 |
| Example 3 | decyl mercaptan | Piperidine (0.2), phosphoric acid (0.15) | 120° C., 2 hours | 99 | 96 |
| Example 4 | dodecyl mercaptan | Piperidine (0.2), propanoic acid (0.1) | 120° C., 2 hours | 98 | 96 |

Test Example 1

Analysis

The thio compounds prepared in Synthesis Example 1, Example 1, Example 3 and Example 4 were analyzed as follows.

1) Elemental Analysis

A Flash EA 1112 Series CHNS—O analyzer (Thermo Electron Co.) was used for elemental analysis of carbon, hydrogen, oxygen, and sulfur. Gases used for the elemental analysis were air, hydrogen gas (99.999%), helium gas (99.9999%), and high-purity oxygen gas (Flex Air). The left furnace was set at 900° C., and the right furnace was set at 680° C. Oven temperature was set at 50° C. Gas flow rate was 130 mL/min for carrier (He) gas, 250 mL/min for oxygen gas, and 100 mL/min for reference (He). BBOT was used as a standard sample for quantification. The result is given in Table 2.

TABLE 2

| | C | H | O | S |
|---|---|---|---|---|
| alkylation products prepared in Synthesis Example 1 | 82.51% | 8.19% | 7.60% | 0.00% |
| octylthio compounds prepared in Example 1 | 77.98% | 9.20% | 6.32% | 4.85% |
| decylthio compounds prepared in Example 3 | 75.83% | 9.82% | 4.89% | 7.59% |
| dodecylthio compounds prepared in Example 4 | 78.23% | 10.17% | 4.70% | 4.62% |

2) Molecular Weight Measurement

Figure 1:
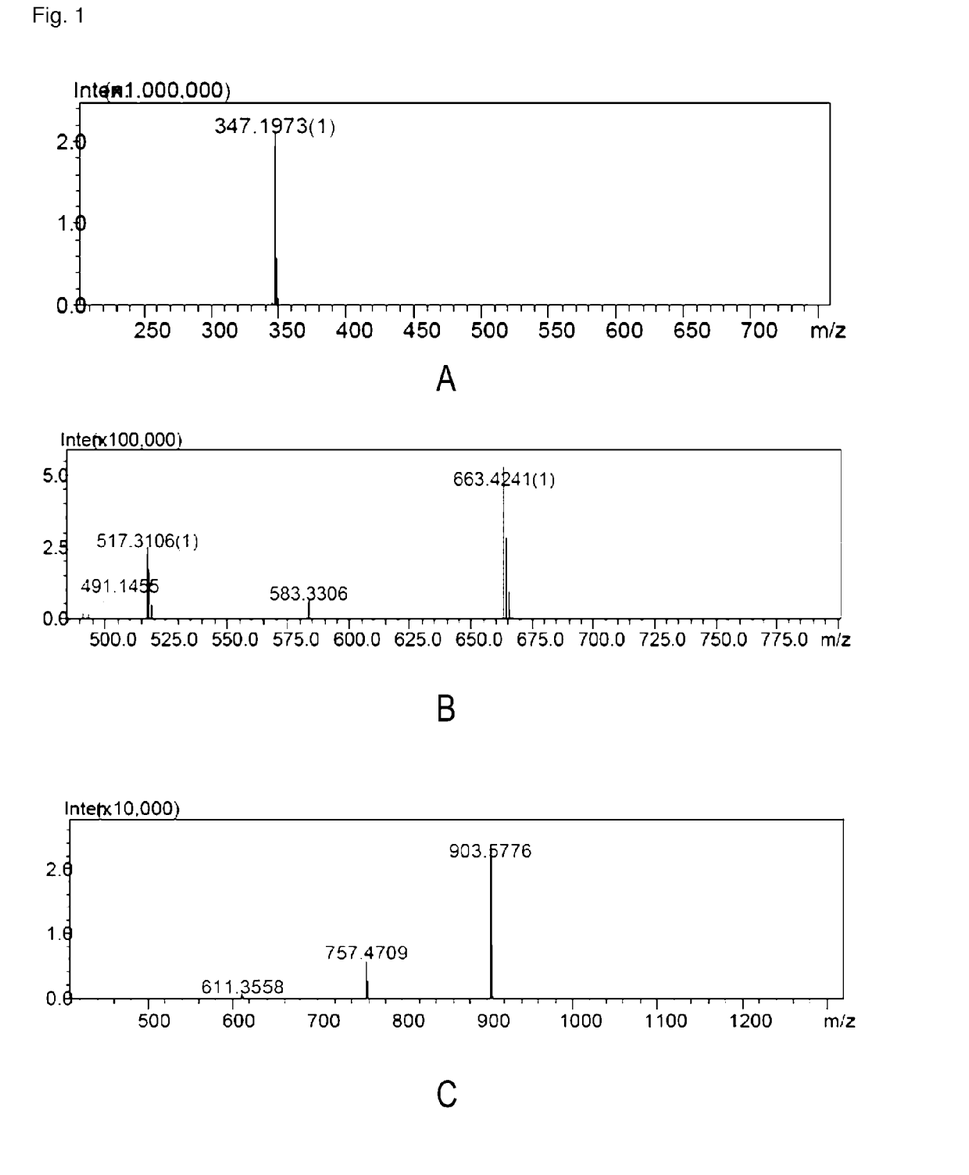
FIG. 1 shows mass spectroscopy (MS) spectra for molecular weight measurement (A: Synthesis Example 1; B, C: Example 1)
Figure 2:
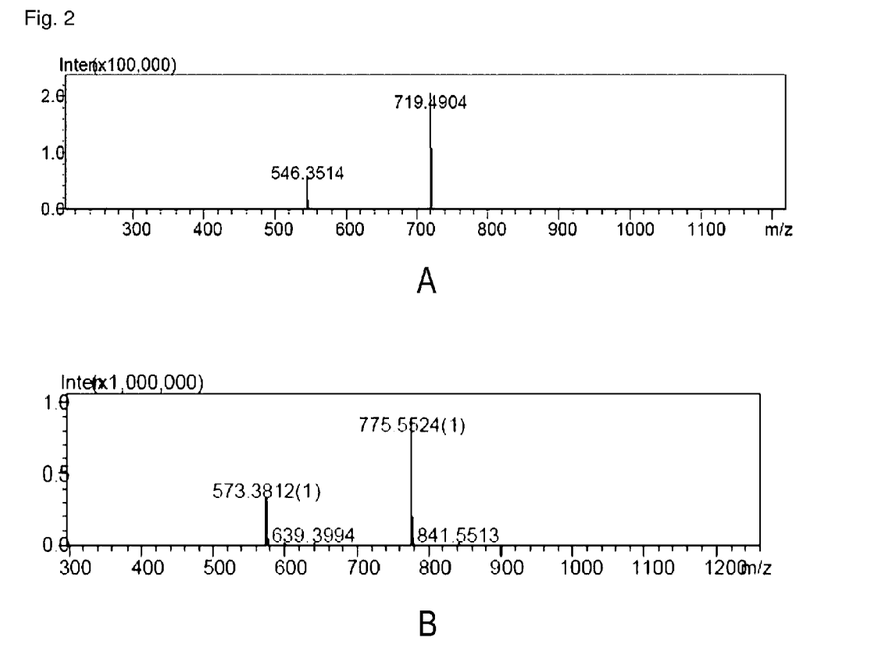
FIG. 2 shows MS spectra for molecular weight measurement (A: Example 3; B: Example 4)
Figure 3:
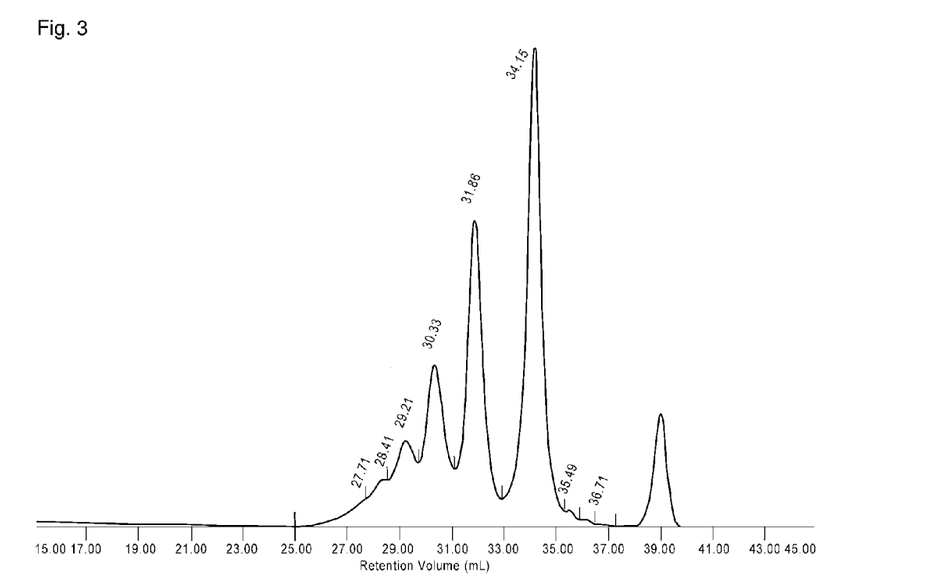
FIG. 3 shows gel permeation chromatography (GPC) spectra for number average molecular weight measurement of alkylation products prepared in Synthesis Example 1.
Figure 4:
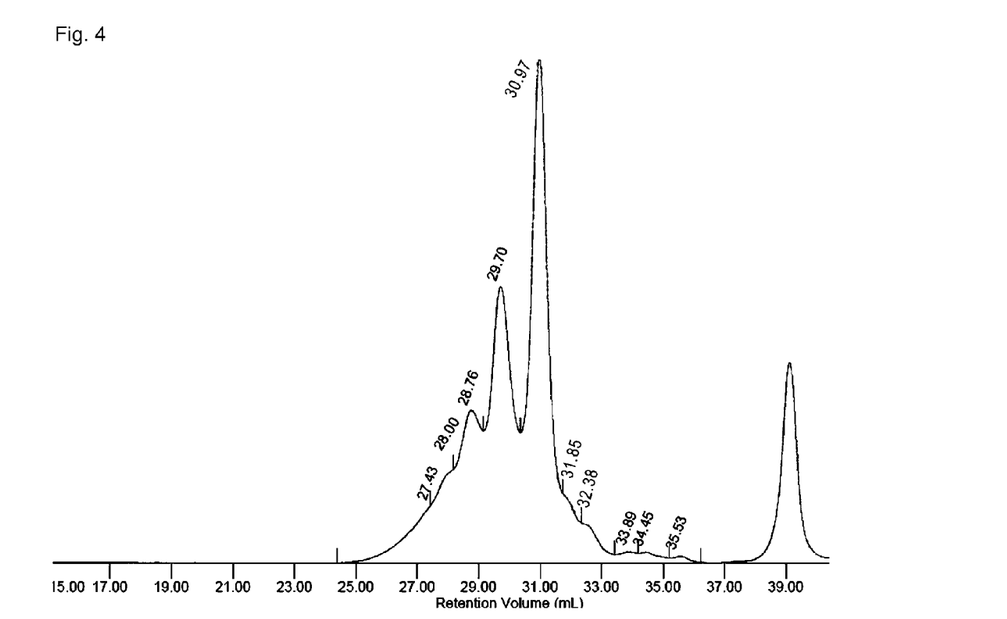
FIG. 4 shows GPC spectra for number average molecular weight measurement of octylthio compounds prepared in Example 1.
Figure 5:
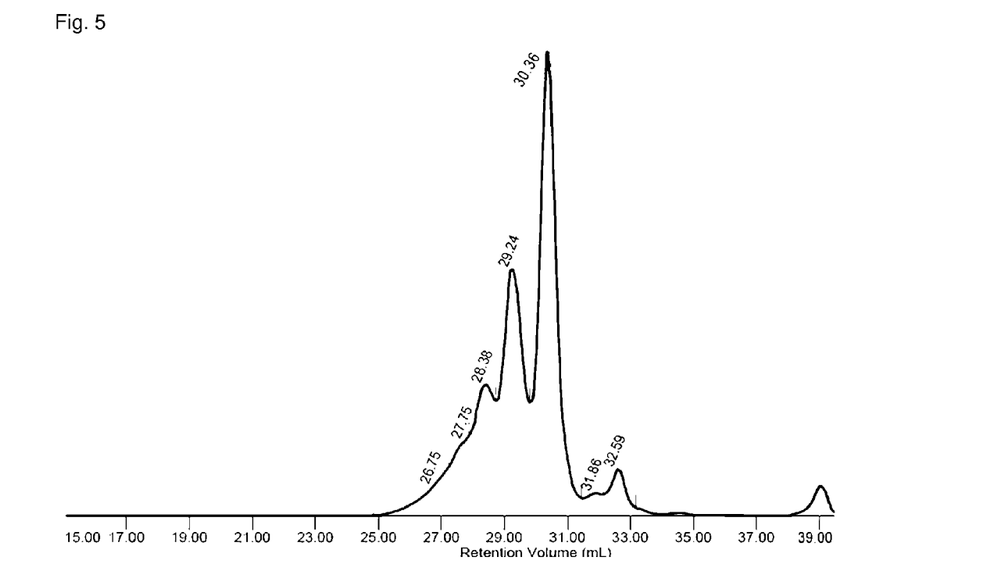
FIG. 5 shows GPC spectra for number average molecular weight measurement of decanylthio compounds prepared in Example 1.
Figure 6:
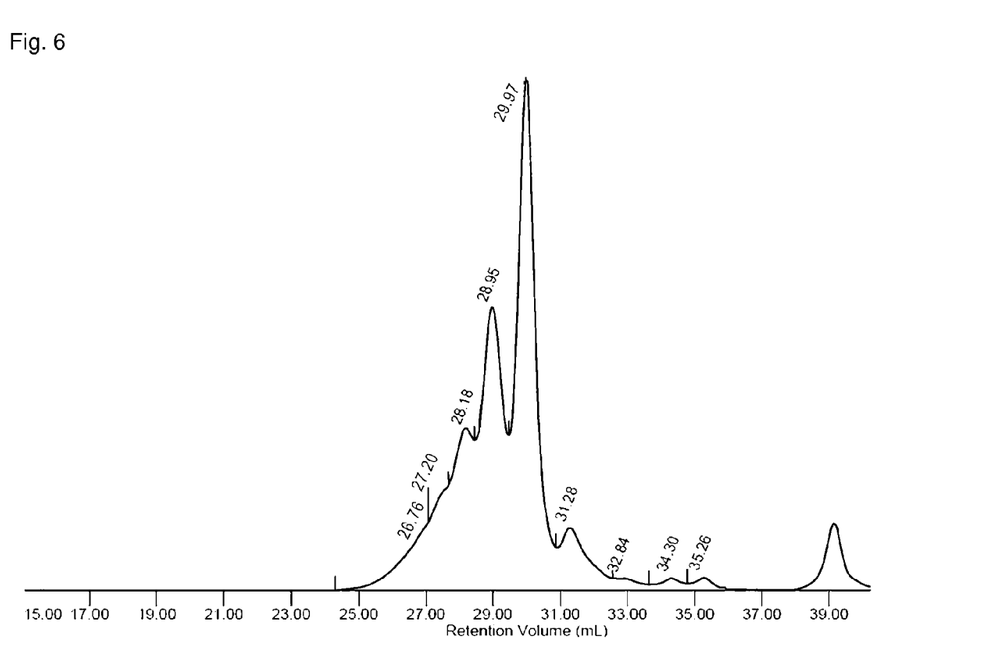
FIG. 6 shows GPC spectra for number average molecular weight measurement of dodecanylthio compounds prepared in Example 1.

LCMS-IT-TOF (Shimadzu Co.) was used for the measurement of molecular weight of compounds. Collision gas used was argon gas and nitrogen gas (99.5% or higher) was used as a nebulizing gas. A liquid chromatography column of a Shiseido Capcell Pak C18 UG120 (2.0 mm, I.D×250 mm) was used. 100% acetonitrile was flown as a mobile phase at a flow rate of 0.2 mL/min. APCI was selected as the ionization mode, and the nebulizing gas flow rate was set at 2.0 L/min. The temperature of APCI probe was set at 400° C., and the CDL at 200° C. The result of analysis was obtained using the LC/MS solution program. The molecular formula was identified using Formula Predictor. The result is given in Table 3 and the MS spectra are shown in FIG. 1.

TABLE 3

| | n | Molecular formula | Molecular weight | [M+] |
|---|---|---|---|---|
| alkylation products prepared in Synthesis Example 1 | 1 | $C_{24}H_{28}O_2$ | 348 | 347 |
| octylthio compounds prepared in Example 1 | 1 | $C_{42}H_{64}O_2S_2$ | 664 | 663, 583, 517, 491 |
| | 2 | $C_{59}H_{84}O_3S_2$ | 904 | 903, 757, 611 |
| decylthio compounds prepared in Example 3 | 1 | $C_{46}H_{72}O_2S_2$ | 720 | 719, 546 |
| dodecylthio compounds prepared in Example 4 | 1 | $C_{50}H_{80}O_2S_2$ | 776 | 775, 573 |

Liquid chromatography (LC) peak analysis revealed that the value of n was 1 or 2 in Example 1. However, n was only 1 for Synthesis Example 1, and Examples 3 and 4. To solve this problem, number average molecular weight ($M_n$) and content of the thio compounds consisted of several oligomers were analyzed by gel permeation chromatography (GPC).

3) Number Average Molecular Weight ($M_n$) Measurement by GPC

A TDA302 detector (Viscotek Co.) and an LC-20AD pump (Shimadzu Co.) were used for GPC. Two OligoPore columns (30 cm, pore size 5 μm, Polymer Laboratories Co.) and G2500HHR and G2000HHR columns (Tosoh Co.) were used. A reflective index (RI) detector was selected. Tetrahydrofuran (THF) was used as a solvent. Flow rate was 1 mL/min. Number average molecular weight ($M_n$) was obtained by using polystyrene as a standard sample. The result is given in Table 4, and the GPC spectra are shown in FIGS. 3 to 6

TABLE 4

| | Peak no. | 1 | 2 | 3 | 4 | 5 | 6 |
|---|---|---|---|---|---|---|---|
| alkylation products prepared in Synthesis Example 1 | $M_n$ | 317 | 604 | 871 | 1,161 | >1,495 | <317 |
| | % | 39.4 | 27.7 | 16.5 | 9.1 | 6.4 | 0.9 |
| octylthio compounds prepared in Example 1 | $M_n$ | 753 | 1,005 | 1,309 | 1,662 | 2,315 | <753 |
| | % | 38.3 | 26.1 | 14.4 | 6.5 | 5.9 | 8.8 |
| decylthio compounds prepared in Example 3 | $M_n$ | 835 | 1,106 | 1,426 | 1,785 | 2,425 | <835 |
| | % | 42.5 | 26.5 | 13.6 | 6.0 | 5.4 | 6.0 |
| dodecylthio compounds prepared in Example 4 | $M_n$ | 942 | 1,223 | 1,550 | 1,909 | 2,581 | <942 |
| | % | 39.2 | 24.9 | 13.1 | 6.1 | 6.2 | 10.5 |
| Value of n in Chemical Formula 1 | | n = 1 | n = 2 | n = 3 | n = 4 | n = 6 | n < 1 |

Peaks 1 to 5 are those of thio compounds comprising p-cresol and dicyclopentadiene at a molar ratio of 2:1, whereas peak 6 is from those p-cresol and dicyclopentadiene at a molar ratio of 1:1 or those comprising p-cresol only.

Preparation Example 1

Preparation of Synthetic Rubber 0.2 g of octylthio compounds prepared in Example 1 was added to 100 g of a butadiene rubber (Kumho KBR 01, raw Mooney viscosity=45, cis content ≥94%) prepared according to a conventional method to give a synthetic rubber.

Comparative Preparation Example 1

0.4 g of 2,6-di-t-butyl-4-methylphenol (BHT), an existing antioxidant, was added to 100 g of a butadiene rubber (Kumho KBR 01, raw Mooney viscosity=45, cis content 94%) prepared according to a conventional method to give a synthetic rubber.

Test Example 2

The solutions of synthetic rubber prepared in Preparation Example 1 and Comparative Preparation Example 1 were stripped by a steam to obtain rubber crumbs, which were then dried on a roll mill at 110° C. to prepare for dried synthetic rubbers. The dried synthetic rubbers were thermally aged at 130° C. for 60 minutes and then Mooney viscosity was measured at 100° C. using Mooney MV 2000 (Alpha Technology). The result is given in Table 5. In Table 5, "$ML_{1+4}$, 100° C." means that Mooney viscosity was measured at 100° C. for 4 minutes after preheating for 1 minute.

TABLE 5

| | Preparation Example 1 | Comparative Preparation Example 1 |
|---|---|---|
| Antioxidant content (phr) | 0.2 | 0.4 |
| Mooney viscosity ($ML_{1+4}$, 100° C.) at 0 hour | 37.7 | 37.8 |
| Mooney viscosity ($ML_{1+4}$, 100° C.) after 4 hours | 33.3 | 26.6 |
| ΔMV | 4.4 | 11.2 |

As shown in Table 5, Preparation Example 1 showed less change in Mooney viscosity (MV) although the antioxidant was used in half the amount as that of Comparative Preparation Example 1. Therefore, it demonstrates that the thio compounds of the present invention have 2 times or better antioxidant effect as compared to BHT, which is the commercially available antioxidant.

INDUSTRIAL APPLICABILITY

As described previously, the thio compounds of the present invention are useful multiple antioxidants acting as both primary- and secondary antioxidants, while solving the volatility problem by increasing molecular weight. Therefore, it may be used as an antioxidant of rubbers and resins.

While the present invention has been described with respect to the specific embodiments, it will be apparent to those skilled in the art that various changes and modifications may be made without departing from the spirit and scope of the invention as defined in the following claims.

What is claimed is:

1. A thio compound represented by Chemical Formula 1:

(1)

wherein $R_1$ is —$CH_2SR_2$, wherein $R_2$ is a linear-, branched-, or cyclic alkyl group of $C_5$-$C_{16}$ or an aromatic group of $C_6$-$C_{16}$; and n is a real number satisfying $1 \leq n \leq 20$.

2. The thio compound according to claim 1, wherein $R_2$ is a linear-, branched- or cyclic alkyl group of $C_6$-$C_{12}$.

3. The thio compound according to claim 1, which has a number average molecular weight of 400 to 5,000.

4. A method of preparing for a thio compound, comprising:
reacting p-cresol with dicyclopentadiene to prepare an alkylation product represented by Chemical Formula 2; and
reacting the alkylation product represented by Chemical Formula 2 with mercaptan represented by $R_2SH$ and paraformaldehyde to prepare a thio compound represented by Chemical Formula 1:

(2)

wherein n is a real number satisfying $1 \leq n \leq 20$; and (1)

where $R_1$ is -$CH_2SR_2$, wherein $R_2$ is a linear-, branched- or cyclic alkyl group of $C_5$-$C_{16}$ or an aromatic group of $C_6$-$C_{16}$; and n is a real number satisfying $1 \leq n \leq 20$.

5. The method according to claim 4, wherein said preparing the alkylation products represented by Chemical Formula 2 comprises performing a Friedel-Crafts alkylation using an acid catalyst selected from:
one or more metal halide(s) selected from $AlCl_3$, $AlBr_3$, $AlI_3$, $TiCl_4$, $SnCl_4$, $FeCl_3$, $ZnCl_2$ and $ZrCl_4$;
one or more inorganic acid(s) selected from $H_2SO_4$, $H_3PO_4$ and HF; and $BF_3$.

6. The method according to claim 4, wherein said preparing the alkylation product represented by Chemical Formula 2 is performed at 25 to 160° C.

7. The method according to claim 4, wherein, in said preparing the alkylation product represented by Chemical Formula 2, p-cresol is used in an equivalent of 1 to 10, based on 1 equivalent of dicyclopentadiene.

8. The method according to claim 4, wherein said preparing the thio compound represented by Chemical Formula 1 is performed in the presence of a base catalyst or a mixture of a base- and an acid catalyst.

9. The method according to claim 8, wherein the base catalyst is one or more selected from dimethylamine, diethylamine, benzylmethylamine, piperidine, pyrrolidine and piperazine.

10. The method according to claim 8, wherein the acid catalyst is:
an aliphatic organic acid or aromatic organic acid having one or more functional group(s) selected from carboxylate, sulfate and phosphate; or
an aliphatic organic acid or aromatic organic acid having one or more functional group(s) selected from alkyl, alkenyl, aryl, hydroxyl, thiol, ether, ester, amide, ketone and aldehyde and one or more functional group(s) selected from carboxylate, sulfate and phosphate within one compound structure.

11. The method according to claim 8, wherein the acid catalyst is one or more heterogeneous acid selected from sulfuric acid, phosphoric acid, and two or more oxygen acids.

12. The method according to claim 4, wherein said preparing the thio compound represented by Chemical Formula 1 is performed in a reaction solvent, the reaction solvent being toluene or a 1: 10 to 100 mixture of water and toluene based on weight.

13. The method according to claim 4, wherein said preparing the thio compound represented by Chemical Formula 1 is performed at 50 to 150° C.

* * * * *